United States Patent [19]

Suzukamo et al.

[11] Patent Number: 4,898,655
[45] Date of Patent: Feb. 6, 1990

[54] METHOD FOR RACEMIZATION OF OPTICALLY ACTIVE CHRYSANTHEMIC ACID OR ITS DERIVATIVES

[75] Inventors: Gohfu Suzukamo, Osaka, Japan; Yoji Sakito, Montreal, Canada; Masami Fukao, Shiga, Japan; Koji Hagiya, Osaka, Japan

[73] Assignee: Sumitomo Chemical Company, Ltd., Osaka, Japan

[21] Appl. No.: 219,761

[22] Filed: Jul. 15, 1988

[30] Foreign Application Priority Data

| Jul. 17, 1987 | [JP] | Japan | 62-179727 |
| Sep. 28, 1987 | [JP] | Japan | 62-245656 |
| Sep. 30, 1987 | [JP] | Japan | 62-248281 |
| Mar. 31, 1988 | [JP] | Japan | 63-82040 |
| Apr. 12, 1988 | [JP] | Japan | 63-89559 |
| Apr. 21, 1988 | [JP] | Japan | 63-99962 |

[51] Int. Cl.$^4$ .............................................. B01J 19/08
[52] U.S. Cl. ............................ 204/157.87; 204/157.88; 204/157.89
[58] Field of Search ................... 204/157.87, 157.88, 204/157.89

[56] References Cited

U.S. PATENT DOCUMENTS

| 3,282,934 | 11/1986 | Matsui et al. | 544/45 |
| 3,657,086 | 4/1972 | Matsui et al. | 204/157.87 |
| 3,989,750 | 11/1976 | Nagase et al. | 562/856 |
| 4,182,906 | 1/1980 | Suzukamo et al. | 562/506 |
| 4,345,090 | 8/1982 | Naumann | 204/157.89 |
| 4,410,721 | 10/1983 | Franck-Neumann | 204/157.88 |
| 4,485,257 | 11/1984 | Suzukamo et al. | 562/401 |
| 4,644,080 | 2/1987 | Suzukamo et al. | 560/124 |
| 4,659,864 | 4/1987 | Suzukamo et al. | 560/124 |
| 4,723,035 | 2/1988 | Suzukamo et al. | 560/124 |

FOREIGN PATENT DOCUMENTS

| 0061880 | 10/1982 | European Pat. Off. |
| 0155765 | 9/1985 | European Pat. Off. |
| 0165070 | 12/1985 | European Pat. Off. |
| 0261824 | 3/1988 | European Pat. Off. |

OTHER PUBLICATIONS

Ueda et al., "Studies on Chrysanthemic Acid ...," Tetrahedron, vol. 27, pp. 2771–2774, 1971.

Primary Examiner—John F. Niebling
Assistant Examiner—Ben C. Hsing
Attorney, Agent, or Firm—Birch, Stewart, Kolasch & Birch

[57] ABSTRACT

Optically active chrysanthemic acid or its derivatives of the formula

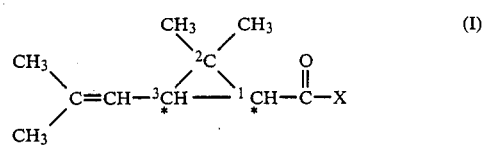

(wherein X represents a hydroxyl group, a halogen atom, a $C_{1-20}$ alkoxy group or a 2,2-dimethyl-3-isobutenyl-cyclopropane carboxyl group and * mark shows asymmetric carbon atom) is racemized by allowing it to react with a bromine compound or a SH compound, in the presence of light.

28 Claims, No Drawings

METHOD FOR RACEMIZATION OF OPTICALLY ACTIVE CHRYSANTHEMIC ACID OR ITS DERIVATIVES

The present invention relates to a method for racemization of optically active chrysanthemic acid or its derivatives. More particularly, it relates to a method for racemization of optically active chrysanthemic acid or its derivatives by allowing optically active chrysanthemic acid or its derivatives of the formula

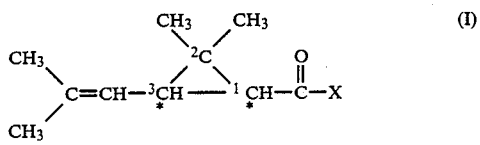

(wherein X represents a hydroxyl group, a halogen atom, a $C_{1-20}$ alkoxy group or a 2,2-dimethyl-3-isobutenylcyclopropane carboxyl group and * mark shows an asymmetric carbon atom) to react, in the presence of light, with at least one bromine compound selected from hydrogen bromide, phosphorus bromide compounds, boron bromide compounds, aluminum bromide compounds, carboxylic acid bromides, tert.carbon-bromine compounds, N-bromine compounds, Si-bromine compounds, S-bromine compounds and halo-bromine compounds, or SH compounds.

Chrysanthemic acid constitutes an acid component of esters well-known as so-called pyrethroid insecticides, such as pyrethrin, allethrin, phthalthrin, etc., which are utilized as low mammalian toxic, quickly effective insecticides, and the chrysanthemic acid derivatives represented by the above formula (I) are useful as intermediates of these pyrethroid insecticides.

The chrysanthemic acid or its derivatives of the above formula (I) has four isomers, that is, two geometrical isomers, i.e., cis and trans forms, each of which respectively has two optical isomers, i.e., (+) and (−) forms. It has been known that, among the isomers, pyrethroid esters composed of the trans-form acid exhibit stronger insecticidal activity than those composed of the corresponding cis-form acid, and the esters composed of (+)-form acid exhibit exceedingly higher activity than those composed of the corresponding (−)-isomer.

Chrysanthemic acid commercially obtained is usually in the form of a mixture of cis and trans forms, each of which is in the form of a racemic modification, namely (±)-form. Optical resolution of the acid by means of an optically active organic base provides the (+)-form acid which is utilized for the preparation of insecticidal compounds having higher activity. The remaining (−)-isomer is little useful as pyrethroid esters. It is a problem to be solved in the production of the pyrethroid ester, particularly in a commercial scale, to racemize the (−)-form acid and convert to more active (±)-form acid, in order to facilitate effective utilization thereof. The racemization of (−)-form acid encounters various difficulties, since there are two asymmetric carbon atoms at $C_1$ and $C_3$ in the cyclopropanecarboxylic acid or its derivatives of the formula (I) above.

Racemization methods of chrysanthemic acids conventionally proposed are (1) oxidation of the $C_3$-isobutenyl group of the acids to convert it to a keto-alcohol group, esterifying the $C_1$-carboxylic acid group, and heating in the presence of metal alcoholate and a solvent (U.S. Pat. No. 3282984) and (2) irradiating (−)-transchrysanthemic acid with ultra-violet ray in the presence of a photosensitizer (U.S. Pat. No. 3657086). The former (1) needs many reaction steps and the latter (2) needs a long time and a large amount of electric energy, since the reaction efficiency is small. Neither of them is hardly carried out in a commercial scale.

The present inventors have provided racemization methods, i.e., (a) converting optically active chrysanthemic acid to the corresponding acid halide and bringing the halide into contact with a Lewis acid, a catalyst (U.S. Pat. Nos. 3989750 and 4182906); (b) allowing optically active cyclopropanecarboxylic anhydride to react with iodine (U.S. Pat. No. 4485257); (c) allowing chrysanthemic acid to react with such a specific catalyst as boron bromide and aluminum bromide (U.S. Pat. Nos. 4644080 and 4659864).

After further extensive study, the present inventors have found that racemization proceeds more favorable than expected by allowing the optically active chrysanthemic acid or its derivatives of the formula (I) above to react, in the presence of light, with hydrogen bromide, phosphorus bromide compounds, boron bromide compounds, aluminum bromide compounds, carboxylic acid bromide compounds, tert.carbon-bromine compounds, N-bromine compounds, Si-bromine compounds, S-bromine compounds, halo-bromine compounds or SH-compounds. The present invention is established on the basis of this finding and additional research.

In the present invention, chrysanthemic acid or its derivatives are able to be converted to the corresponding racemic form without once converting the starting compounds to the other derivatives, no matter what the starting compounds may be, acid themselves, acid halides thereof, esters thereof or acid anhydride thereof. In other words, chrysanthemic acid or (−)-chrysanthemic acid esters which have been separated from various optical resolutions, or (−)-chrysanthemic acid halides, intermediates thereof, are utilized with efficiency. Furthermore, racemic acid or its derivatives obtained are rich in a trans isomer which is more effective.

The present method is also utilized as a method in which racemic cis isomer or a mixture of racemic cis and racemic trans isomers of chrysanthemic acid or its derivatives is converted to the racemic trans isomer-rich form.

The method of the present invention will more fully be described hereafter.

The optically active chrysanthemic acid or its derivatives represented by formula (I) which are the starting materials in the present invention include such optically active compounds as chrysanthemic acid, chrysanthemic acid chloride, chrysanthemic acid bromide, methyl chrysanthemate, ethyl chrysanthemate, propyl chrysanthemate, butyl chrysanthemate, cyclohexyl chrysanthemate, cyclohexyl methyl chrysanthemate, benzyl chrysanthemate and chrysanthemic anhydride.

In the present invention, any of the four isomers of chrysanthemic acid or its derivatives are used solely or in mixtures of isomers at optional ratios. Any degree of optical purity may be used. Needless to say, however, it is preferred to use chrysanthemic acid or its derivatives of (−)-form or rich in (−)-form.

Bromine compounds usable are selected from hydrogen bromide, phosphorus bromide compounds, boron bromide compounds, aluminum bromide compounds, carboxylic acid bromide compounds, tert.carbon-bromine compounds, N-bromine compounds, Si-bromine compounds, S-bromine compounds and halo-bromine compounds. Hydrogen bromide used may be in the form of a gas or a solution in a solvent or may be produced in situ from a bromide such as lithium bromide or sodium bromide and an acid such as sulfuric acid. Phosphorus bromide compounds include phosphorus tribromide, phosphorus pentabromide and phosphorus oxybromide. Boron bromide and aluminum bromide include boron tribromide and aluminum tribromide. These boron and aluminum bromides may be in the form of a complex with a small amount of water, acids, alcohols or ethers.

Carboxylic acid bromides are usually those having 1–18 carbon atoms. They include, for example, aliphatic monocarbonyl bromides such as acetyl bromide, propionyl bromide, butyryl bromide, isobutyryl bromide, valeryl bromide, isovaleryl bromide, pivaloyl bromide, hexanoyl bromide, heptanoyl bromide, cyclohexanecarbonyl bromide, octanoyl bromide, nonanoyl bromide, decanoyl bromide, 3-(2-methylpropenyl)-2,2-dimethylcyclopropanecarbonyl bromide, undecanoyl bromide, palmitoyl bromide and stearoyl bromide; aliphatic dicarboxylic acid dibromides such as malonyl dibromide, succinyl dibromide, glutaryl dibromide, adipoyl dibromide, pimeloyl dibromide, suberoyl dibromide, azelaoyl dibromide and sebacoyl dibromide; acid bromides of mono and dicarboxylic acids having an aromatic group such as benzoyl bromide, phenylacetyl bromide, phenylpropionyl bromide, phenylbutyryl bromide, naphthalenecarbonyl bromide, phthaloyl dibromide, terephthaloyl dibromide and isophthaloyl dibromide.

Tert.carbon-bromide compounds include those of $C_{3-19}$ such as t-butyl bromide, 1-bromonorbornane, 1-bromoadamantane, 1-bromo-1-methylcyclohexane, 1-bromo-1-methylcyclopentane, 2-bromo-2-methylbutane, 3-bromo-3-methylpentane, 3-bromo-3-ethylpentane and triphenyl methylbromide.

N-bromine compounds are, for example, N-bromoimides such as N-bromosuccinimide, and N-bromoamides such as N-bromoacetamide, N-bromopropionamide, N-bromobutylamide and N-bromovaleramide.

Si-bromine compounds are lower alkylsilyl bromides such as trimethylsilyl bromide, dimethylsilyl dibromide, methylsilyl tribromide, triethylsilyl bromide, diethylsilyl dibromide and dimethyl-t-butylsilyl bromide; and silyl tetrabromide.

S-bromine compounds are, for example, thionyl bromide, sulfuryl bromide, aryl sulfonyl bromides such as p-toluene-sulfonyl bromide, alkylsulfonyl bromides such as methanesulfonyl bromide, and arylsulfenyl bromides such as phenylsulfenyl bromide.

Halo-bromine compounds are, for example, bromine, iodine monobromide and iodine tribromide.

Among these bromine compounds, preferred are hydrogen bromide, phosphorus bromide compounds, boron bromide compounds and aluminum bromide compounds.

The bromine compounds are usually within the range of 1/1000–⅓ mol, preferably 1/100–1/7, per mol of chrysanthemic acid or its derivatives to be treated, although the amount varies depending on varieties thereof.

SH compounds may be any of those containing a —SH group. Thiols, carbothioic acids and dithioic acids are usually used. They are, for example, aromatic thiols such as thiophenol, o-, m- and p-thiocresols, o-, m- and p-methoxybenzene thiols, 1- and 2-naphthalenethiols, dithiocatechol, dithioresorcin and dithiohydro quinone; alkyl thiols such as methanethiol, ethanethiol, 1-propanethiol, 2-propanethiol, butanethiol, pentanethiol, hexanethiol, heptanethiol, octanethiol, nonanethiol, decanethiol, dodecanethiol, dithiothritol, dithio erythritol and butanedithiol; thiolcarboxylic acids such as thioglycolic acid, thiosalicylic acid, thiolactic acid and thiomalic acid; thiocarboxylic acids such as thioacetic acid, thiopropionic acid, thiobutyric acid and thiobenzoic acid and dithio acids such as dithioacetic acid, dithiopropionic acid, dithiobutyric acid and dithiobenzoic acid.

SH-compounds are used in an amount within the range of 1/1000–⅓ mol, per mol of chrysanthemic acid or its derivatives to be treated.

The present invention is featured in that the bromine compound or SH-compound above mentioned is allowed to react in the presence of light. A light source which emits ultra-violet ray of 200–400 nm, such as a high pressure mercury lamp, a xenon lamp, a low pressure mercury lamp and solar light, may be used.

The present racemization reaction is preferably carried out in the presence of an inert solvent. The solvents include saturated aliphatic hydrocarbons, aromatic hydrocarbons and their halide compounds, ethers, etc. These solvents are usually used in an amount of 0.5–100 times preferably 1.5–50 times by weight, as much as the chrysanthemic acid or its derivatives to be treated.

Reaction temperature is usually from −30° C. to the boiling point of the chrysanthemic acid or its derivatives or the boiling point of the solvent when it is employed. A preferable temperature is usually −20° C. to 80° C. and 50° to 140° C.

In carrying out the method of the present invention, the chrysanthemic acid or its derivatives and a bromine compound or a SH-compound are mixed in the presence of a solvent and then thereto irradiation with a light source is performed. Alternatively, chrysanthemic acid or its derivatives are dissolved in a solvent and then thereinto a solution of hydrogen bromide is added dropwise under irradiation. Period of irradiation is usually from that required for addition of a catalyst to ten hours after the addition is completed.

Progress of the reaction is determined by sampling a part of a reaction mixture and assaying optical rotation thereof or analysis by gas chromatography.

Thus, racemized chrysanthemic acid or its derivatives are prepared. According to the present invention, any of optically active chrysanthemic acid, esters, acid halides or acid anhydrides are converted into the corresponding racemic form with high efficiency without once converting the starting compounds to another derivative. Furthermore, racemic cis isomer or a mixture of racemic cis and trans isomers is able to be converted to racemic trans rich isomer.

The following examples will further explain the present invention.

EXAMPLE 1

To a solution of levo-rotatory chrysanthemic acid (10 g, composition: (+)-cis, 3.0%; (−)-cis, 18.8%; (+)-trans, 10.2%; and (−)-trans, 68.0%) in toluene (17 ml) was added dropwise for 40 minutes 25% hydrogen bromide (2.25 g) and toluene (7.5 g) under irradiation with a xenon lamp (500 W, Pyrex glass filter) at room temperature under a nitrogen atmosphere with stirring.

After the addition was over, dilute hydrochloric acid was added, and the mixture was stirred and subjected to separation into two layers. The organic layer was extracted with 10% aqueous caustic soda solution (29 g). To the aqueous layer was added dilute sulfuric acid until the layer became acid and it was extracted twice with toluene. The toluene layer was washed with water and subjected to distillation under reduced pressure to remove the solvent. The residual solution was further distilled to obtain a fraction (boiling point: 110°–119° C./2.5 mm Hg, 9.6 g). IR spectrum showed that the fraction consisted of chrysanthemic acid. A part of the reaction mixture was sampled and converted to ester with (+)-2-octanol. Gas chromatography assay gave the following optical isomer ratio: (+)-cis, 2.5%; (−)-cis, 2.4%; (+)-trans, 45.4%; and (−)-trans, 49.7%.

EXAMPLE 2

To a solution of the same levo-rotatory chrysanthemic acid (1 g) as used in Example 1 in toluene (10 g) was added 7 wt % hydrogen bromide-toluene solution (690 mg) at room temperature under a nitrogen atmosphere. Irradiation with a xenon lamp (500 W, Pyrex glass filter) was made for 30 minutes under stirring.

After the irradiation was over, similar treatment as in Example 1 was applied to obtain chrysanthemic acid (0.94 g). Optical isomer ratio of the product was (+)-cis, 3.0%; (−)-cis, 2.9%; (+)-trans, 45.2%; and (−)-trans, 48.9%.

EXAMPLE 3

Example 2 was repeated except that phosphorus tribromide (160 mg) in place of the hydrogen bromide-toluene solution, to obtain chrysanthemic acid (0.90 g). The optical isomer ratio of the product was (+)-cis, 6.5%; (−)-cis, 6.5%; (+)-trans, 43.2%; and (−)-trans, 43.8%.

EXAMPLE 4

To a solution of the same levo-rotatory chrysanthemic acid (10 g) as in Example 1 in toluene (90 g) was added dropwise boron tribromide (0.85 g) at room temperature under a nitrogen atmosphere with stirring. Irradiation with a high pressure mercury lamp (110 W) was made for 30 minutes.

After the reaction was over, similar after-treatment as in Example 1 was applied to obtain chrysanthemic acid (8.5 g). The optical isomer ratio of the product was (+)-cis, 2.7%; (−)-cis, 2,9%; (+)-trans, 45.8%; and (−)-trans, 48.6%.

EXAMPLE 5

To a solution of (+)-cis chrysanthemic acid (2.0 g) in toluene (18 ml) was added a solution of boron tribromide (13 mg) in toluene (2.2 ml) at room temperature under a nitrogen atmosphere. Irradiation with a high pressure mercury lamp (100 W) was made for 10 minutes under stirring. After the reaction was over, similar after-treatment as in Example 1 was applied to obtain chrysanthemic acid (1.98 g). The optical isomer ratio of the product was (+)-cis, 3.5%; (−)-cis, 3.2%; (+)-trans, 46.5%; and (−)-trans, 46.8%.

EXAMPLE 6

To a solution of (+)-cis chrysanthemic acid (2.0 g) in toluene (20 ml) was added a solution of aluminum tribromide (32 mg) in toluene (2.2 ml) at room temperature under a nitrogen atmosphere. Irradiation with a xenon lamp (500 W) was made for 10 minutes under stirring. After the irradiation was over, the similar after-treatment as in Example 1 was applied to obtain chrysanthemic acid (1.97 g). The optical isomer ratio of the product was (+)-cis, 3.7%; (−)-cis, 3.1%; (+)-trans, 46.6%; and (−)-trans, 46.6%.

EXAMPLE 7

To a solution of the same levo-rotatory chrysanthemic acid (10 g) as in Example 1 in toluene (90 g) was added a solution of aluminum tribromide (0.2 g) and dioxane (2.4 g) at room temperature under a nitrogen atmosphere. Irradiation with a high pressure mercury lamp (100 W) was made for 30 minutes. After the irradiation was over, similar after-treatment as in Example 1 was applied to obtain chrysanthemic acid (9.4 g). The optical isomer ratio of the product was (+)-cis, 3.9%; (−)-cis, 4.9%; (+)-trans, 30.5%; and (−)-trans, 60.7%.

EXAMPLE 8

Example 2 was repeated except that acetylbromide (220 mg) was used in place of the hydrogen bromide-toluene solution, to obtain chrysanthemic acid (0.95 g). The optical isomer ratio of the product was (+)-cis, 5.2%; (−)-cis, 4.9%; (+)-trans, 43.0%; and (−)-trans, 46.9%.

EXAMPLE 9

Example 2 was repeated except that bromine (152 mg) was used in place of the hydrogen bromide-toluene solution, to obtain chrysanthemic acid (0.79 g). The optical isomer ratio of the product was (+)-cis, 2.9%; (−)-cis, 2.8%; (+)-trans, 42.1%; and (−)-trans, 52.2%.

EXAMPLE 10

To a solution of levo-rotatory chrysanthemic acid (10 g, composition, (+)-cis, 2.3%; (−)-cis, 15.7%; (+)-trans, 9.6%; and (−)-trans, 72.4%) in chlorobenzene (9 g) was added thiophenol (65 mg). Irradiation with a high pressure mercury lamp (100 W) was made for 3 hours.

After the reaction was over, similar after-treatment was applied to obtain chrysanthemic acid (0.94 g). The optical isomer ratio of the product was (+)-cis, 3.2%; (−)-cis, 3.8%; (+)-trans, 41.1%; and (−)-trans, 51.9%.

EXAMPLE 11

To a solution of (+)-cis chrysanthemic acid (1.0 g) in toluene (9 g) was added n-butanethiol (107 mg). Irradiation with a high pressure mercury lamp (100 W) was made for one hour. After the reaction was over, similar after-treatment as in Example 1 was applied to obtain chrysanthemic acid (0.9 g). The optical isomer ratio of the product was (+)-cis, 3.0%; (−)-cis, 2.1%; (+)-trans, 46.6%; and (−)-trans, 48.3%.

EXAMPLE 12

To a solution of levo-rotatory ethyl chrysanthemate (10 g, composition: (+)-cis, 2.5%; (−)-cis, 14.7%; (+)-trans, 11.9%; and (−)-trans, 70.9%) in toluene (50 ml) was added dropwise for 30 minutes a solution of 25% hydrogen bromide-acetic acid (2.5 g) and toluene (8 g) under irradiation with a xenon lamp (500 W, Pyrex glass filter) at room temperature under a nitrogen atmosphere with stirring.

After the addition was over, aqueous sodium hydroxide solution (2%) was added until neutralization was obtained, and the mixture was subjected to distillation under reduced pressure to remove the solvent. The residual solution was extracted with hexane and aqueous caustic soda solution (2%). The organic layer was washed with water and subjected to concentration under reduced pressure and to distillation until a fraction (boiling point: 85°–88° C./10 mm Hg, 9.4 g) was obtained. IR spectrum showed that the fraction consisted of ethyl chrysanthemate. A part of the reaction mixture was hydrolyzed in a usual manner and the resulting carboxylic acid was converted to ester with (+)-2-octanol. Gas chromatography assay gave the following optical isomer ratio: (+)-cis, 2.3%; (−)-cis, 2.7%; (+)-trans, 44.9%; and (−)-trans, 50.1%.

EXAMPLE 13

To a solution of the same levo-rotatory ethyl chrysanthemate (10 g) as used in Example 12 in toluene (90 g) was added boron tribromide (0.18 g) at room temperature under a nitrogen atmosphere. Irradiation with a high pressure mercury lamp (110 W) was made for 30 minutes. After the reaction was over, similar after-treatment as in Example 12 was applied to obtain chrysanthemic acid (9.6 g). The optical isomer ratio of the product was (+)-cis, 4.0%; (−)-cis, 2.6%; (+)-trans, 42.5%; and (−)-trans, 50.9%.

EXAMPLE 14

To a solution of the same levo-rotatory ethyl chrysanthemate (10 g) as used in Example 12 in dioxane (90 g) was added aluminum tribromide (1.02 g) at room temperature under a nitrogen atmosphere. Irradiation with a high pressure mercury lamp (110 W) was made for 30 minutes. After the reaction was over, similar after-treatment as in Example 12 was applied to obtain ethyl chrysanthemate (8.6 g). The optical isomer ratio of the product was (+)-cis, 2.6%; (−)-cis, 2.6%; (+)-trans, 47.1%; and (−)-trans, 47.7%.

EXAMPLE 15

To a solution of the same ethyl chrysanthemate (0.5 g) as used in Example 12 in toluene (5 g) was added t-butyl bromide (50 mg) at room temperature under a nitrogen atmosphere. Irradiation with a xenon lamp (500 W, Pyrex glass filter) was made for one hour under stirring. After the irradiation was over, similar after-treatment as in Example 12 was applied to obtain ethyl chrysanthemate (0.43 g). The optical isomer ratio of the product was (+)-cis, 6.4%; (−)-cis, 6.5%; (+)-trans, 33.2%; and (−)-trans, 53.9%.

EXAMPLE 16

Example 15 was repeated except that trimethylsilyl bromide (40 mg) was used in place of the t-butyl bromide, to obtain ethyl chrysanthemate (0.49 g). The optical isomer ratio of the product was (+)-cis, 3.3%; (−)-cis, 3.4%; (+)-trans, 31.1%; and (−)-trans, 62.2%.

EXAMPLE 17

Example 15 was repeated except that thionyl bromide (100 mg) was used in place of the t-butyl bromide, to obtain ethyl chrysanthemate (0.38 g). The optical isomer ratio of the product was (+)-cis, 3.7%; (−)-cis, 3.7%; (+)-trans, 34.8%; and (−)-trans, 57.8%.

EXAMPLE 18

Example 15 was repeated except that N-bromoacetamide (50 mg) was used in place of the t-butyl bromide, to obtain ethyl chrysanthemate (0.48 g). The optical isomer ratio of the product was (+)-cis, 2.7%; (−)-cis, 2.7%; (+)-trans, 39.7%; and (−)-trans, 54.9%.

EXAMPLE 19

To a solution of levo-rotatory ethyl chrysanthemate (10 g, composition: (+)-cis, 2.4%; (−)-cis, 14.9%; (+)-trans, 9.3%; and (−)-trans, 73.4%) in 1,2-dichloroethane (9 g) was added thiocresol (63 mg) and irradiation with a high pressure mercury lamp (100 W) was made for 5 hours.

After the reaction was over, extraction was made with aqueous sodium hydroxide solution (2%). The organic layer was washed with water and then subjeted to concentration under reduced pressure and distillation to obtain a fraction (boiling point: 85°–88° C./10 mm Hg, 0.97 g). IR spectrum showed that the fraction consisted of ethyl chrysanthemate. A part of the fraction was hydrolyzed in a usual manner and converted to ester with (+)-2-octanol. Gas chromatography assay gave the following optical isomer ratio: (+)-cis, 3.4%; (−)-cis, 3.3%; (+)-trans, 33.6%; and (−)-trans, 59.7%.

EXAMPLE 20

To a solution of (+)-cis ethyl chrysanthemate (1.0 g) in 1,2-dichloroethane (9.0 g) was added thiobenzoic acid (108 mg). Irradiation with a xenon lamp (500 W) was made for three hours. After the reaction was over, similar after-treatment as in Example 19 was applied to obtain ethyl chrysanthemate (0.94 g). The optical isomer ratio of the product was (+)-cis, 33.4%; (−)-cis, 4.9%; (+)-trans, 30.7%; and (−)-trans, 31.0%.

EXAMPLE 21

To a solution of levo-rotatory chrysanthemic acid chloride (1 g, composition: (+)-cis, 2.5%; (−)-cis, 14.8%; (+)-trans, 11.9%; and (−)-trans, 70.8%) in benzene (10 g) was added bromine (90 mg) at room temperature under a nitrogen atmosphere and irradiation with a xenon lamp (500 W, Pyrex glass filter) was made for 30 minutes.

After the irradiation was over, benzene was concentrated and distilled to obtain a fraction (boiling point: 72°–78° C./2 mm Hg, 0.8 g) of chrysanthemic acid chloride. After the acid chloride was converted to ester with (+)-2-octanol in a usual manner. Gas chromatography assay gave the following optical isomer ratio: (+)-cis, 4.4%; (−)-cis, 4.3%; (+)-trans, 44.9%; and (−)-trans, 46.4%.

EXAMPLE 22

Example 21 was repeated except that phosphorus tribromide (79 mg) was used in place of bromine, to obtain chrysanthemic acid chloride (0.9 g). The optical isomer ratio of the product was (+)-cis, 4.8%; (−)-cis, 5.7%; (+)-trans, 40.3%; and (−)-trans, 49.2%.

EXAMPLE 23

Example 21 was repeated except that tetrabromosilane (190 mg) was used in place of the bromine, to obtain chrysanthemic acid chloride. The optical isomer ratio of the product was (+)-cis, 9.3%; (−)-cis, 13.2%; (+)-trans, 35.5%; and (−)-trans, 42.0%.

EXAMPLE 24

To a solution of levo-rotatory chrysanthemic acid chloride (1.0 g, composition: (+)-cis, 2.4%; (−)-cis, 14.9%; (+)-trans, 9.3%; and (−)-trans, 73.4%) in chlorobenzene (9.0 g) was added thiophenol (89 mg). Irradiation with a high pressure mercury lamp (100 W) was made for 3 hours. After the reaction was over, a part of the reaction solution was converted to ester with (+)-2-octanol. Gas chromatography assay gave the following optical isomer ratio: (+)-cis, 4.9%; (−)-cis, 9.5%; (+)-trans, 30.1%; and (−)-trans, 55.5%.

EXAMPLE 25

To a solution of (−)-cis chrysanthemic acid chloride (1.0 g) in chlorobenzene (9.0 g) was added thiosalicylic acid (125 mg). Irradiation with a xenon lamp (500 W) was made for 3 hours. After the reaction was over, a part of the reaction solution was sampled and converted to ester with (+)-2-octanol. Gas chromatography assay gave the following optical isomer ratio: (+)-cis, 4.3%; (−)-cis, 16.4%; (+)-trans, 40.0%; and (−)-trans, 39.3%.

EXAMPLE 26

To a solution of levo-rotatory chrysanthemic anhydride (1.45 g, composition: (+)-cis, 1.8%; (−)-cis, 17.6%; (+)-trans, 10.1%; and (−)-trans, 70.5%) in toluene (13 g) was added phosphorus tribromide (0.37 g) under a nitrogen atmosphere. Irradiation with a xenon lamp (500 W) was made for one hour under heating and stirring. After the irradiation was over, a part of the reaction solution was sampled, hydrolyzed and converted to ester with (+)-2-octanol. The optical isomer ratio of chrysanthemic acid in the product was (+)-cis, 2.8%; (−)-cis, 6.7%; (+)-trans, 29%; and (−)-trans, 61.5%.

EXAMPLE 27

To a solution of the same levo-rotatory chrysanthemic anhydride (2.05 g) as in Example 26 in toluene (18 g) was added thiocresol (240 mg) under a nitrogen atmosphere. Irradiation with a high pressure mercury lamp (100 W) was made for one hour at 80° C. under stirring. After the irradiation was over, similar after-treatment as in Example 26 was applied. The optical isomer ratio of the product was (+)-cis, 2.5%; (−)-cis, 3.5%; (+)-trans, 33.0%; and (−)-trans, 61.0%.

EXAMPLE 28

To a solution of cis chrysanthemic acid (10 g) in toluene (53 ml) was added a solution of 25% hydrogen bromide-acetic acid (1.3 g) at room temperature under a nitrogen atmosphere. Irradiation with a high pressure mercury lamp (110 W) was made for 30 minutes under stirring. After the irradiation was over, similar after-treatment as in Example 1 was applied to obtain chrysanthemic acid (9.6 g). Gas chromatography assay of the product gave the isomer ratio: cis, 8.6%; and trans, 91.4%.

EXAMPLE 29

To a solution of cis chrysanthemic acid (1.0 g) in toluene (9 g) was added phosphorus tribromide (0.11 g) at room temperature under a nitrogen atmosphere. Irradiation with a xenon lamp (500 W, Pyrex glass filter) was made for 30 minutes under stirring. After the irradiation was over, similar after-treatment as in Example 1 was applied to obtain chrysanthemic acid (0.90 g). The isomer ratio of the product was: cis, 10.0%; and trans, 90.0%.

EXAMPLE 30

To a solution of cis chrysanthemic acid (2.0 g) in toluene (18 ml) was added a solution of boron tribromide (13 mg) in toluene (2.2 ml) at room temperature under a nitrogen atmosphere. Irradiation with a high pressure mercury lamp (100 W) was made for 10 minutes under stirring. After the reaction was over, similar after-treatment as in Example 1 was applied to obtain chrysanthemic acid (1.98 g). A part of the reaction solution was converted to ethyl ester. Gas chromatography assay gave the isomer ratio of the product: cis, 6.8%; and trans, 93.2%.

EXAMPLE 31

To a solution of cis chrysanthemic acid (2.0 g) in toluene (20 ml) was added a solution of aluminum tribromide (32 mg) in toluene (2.2 ml) at room temperature under a nitrogen atmosphere. Irradiation with a xenon lamp (500 W) was made for 10 minutes under stirring. After the irradiation was over, similar after-treatment as in Example 30 was applied to obtain chrysanthemic acid (1.97 g). The isomer ratio of the product was cis, 6.8%; and trans, 93.2%.

EXAMPLE 32

To a solution of chrysanthemic acid (1.0 g, composition: cis, 21.8%; and trans, 78.2%) in toluene (13 ml) was added acetyl bromide (220 mg) at room temperature under a nitrogen atomsphere. Irradiation with a xenon lamp (500 W, Pyrex glass filter) was made for 30 minutes under stirring. After the irradiation was over, similar after-treatment as in Example 1 was applied to obtain chrysanthemic acid (0.95 g). The isomer ratio of the product was cis, 10.1%; and trans, 89.9%.

EXAMPLE 33

Example 32 was repeated except that bromine (152 mg) was used in place of the acetyl bromide, to obtain chrysanthemic acid (0.79 g). The isomer ratio of the product was cis, 5.7% and trans, 94.3%.

EXAMPLE 34

To a solution of cis chrysanthemic acid (1.0 g) in toluene (9 g) was added butanethiol (107 mg). Irradiation with a high pressure mercury lamp (100 W) was made for one hour. After the reaction was over, similar after-treatment as in Example 1 was applied to obtain chrysanthemic acid (0.9 g). A part of the product was converted to ethyl ester in a usual manner. Gas chromatography assay of the product gave the following isomer ratio: cis, 5.2%; and trans, 94.8%.

EXAMPLE 35

To a solution of chrysanthemic acid (1.0 g, composition: cis, 18.2%; and trans, 81.8%) in chlorobenzene (9 g) was added thiophenol (65 mg). Irradiation with a high pressure mercury lamp (100 W) was made for 3 hours. After the reaction was over, similar after-treatment as in Example 34 was applied to obtain chrysanthemic acid (0.94 g). The isomer ratio of the product was cis, 6.9%; and trans, 93.1%.

EXAMPLE 36

To a solution of ethyl chrysanthemate (10 g, composition: cis, 17.2% and trans, 82.8%) in toluene (50 ml) was added dropwise over 30 minutes a solution of 25% hydrogen bromide-acetic acid (2.5 g) and toluene (8 g)

at room temperature under a nitrogen atmosphere with stirring, while irradiation with a xenon lamp (500 W, Pyrex glass filter) was made. After the reaction was over, similar after-treatment as in Example 12 was applied to obtain ethyl chrysanthemate (9.4 g). Gas chromatography assay gave the isomer ratio: cis, 5.0%; and trans, 95.0%.

EXAMPLE 37

To a solution of ethyl chrysanthemate (2.0 g, composition: cis, 88.7% and trans, 11.3%) in dioxane (20 ml) was added a solution of boron tribromide (26 mg) in dioxane (2.3 ml) at room temperature under a nitrogen atmosphere. Irradiation with a high pressure mercury lamp (100 W) was made for one hour under stirring. After the irradiation was over, similar after-treatment as in Example 12 was applied to obtain ethyl chrysanthemate (1.95 g). The isomer ratio of the product was cis, 5.4%; and trans, 94.6%.

EXAMPLE 38

To a solution of the same ethyl chrysanthemate (2.0 g) as in Example 37 in dioxane (20 ml) was added a solution of aluminum tribromide (55 mg) in dioxane (2.3 ml) at room temperature under a nitrogen atmosphere. Irradiation with a high pressure mercury lamp (100 W) was made for 3 hours under stirring. After the reaction was over, simialr after-treatment as in Example 12 was applied to obtain ethyl chrysanthemate (1.91 g). The isomer ratio of the product was cis, 15.4%; and trans, 84.6%.

EXAMPLE 39

To a solution of the same ethyl chrysanthemate (0.5 g) as in Example 36 in toluene (5 g) was added t-butyl bromide (50 mg) at room temperature under a nitrogen atmosphere. Irradiation with a xenon lamp (500 W, Pyrex glass filter) was made for one hour under stirring. After the irradiation was over, similar after-treatment as in Example 12 was applied to obtain ethyl chrysanthemate (0.43 g). The isomer ratio of the product was cis, 12.9%; and trans, 87.1%.

EXAMPLE 40

Example 39 was repeated except that trimethylsilyl bromide (40 mg) was used in place of the t-butyl bromide to obtain ethyl chrysanthemate (0.49 g). The isomer ratio of the product was cis, 6.7% and trans 93.3%.

EXAMPLE 41

Example 39 was repeated except that thionyl bromide (10 mg) was used in place of the t-butyl bromide to obtain ethyl chrysantemate (0.38 g). The isomer ratio of the product was cis, 7.4% and trans, 92.6%.

EXAMPLE 42

Example 39 was repeated except that N-bromoacetamide (50 mg) was used in place of the t-butyl bromide to obtain ethyl chrysantemate (0.48 g). The isomer ratio of the product was cis, 5.4% and trans, 94.6%.

EXAMPLE 43

To a solution of ethyl chrysanthemate (1.0 g, composition: cis, 17.3% and trans, 82.7%) in 1,2-dichloroethane (9 g) was added thiocresol (63 mg). Irradiation with a high pressure mercury lamp (100 W) was made for 5 hours. After the reaction was over, similar after-treatment as in Example 19 was applied to obtain ethyl chrysanthemate (0.97 g). Gas chromatography assay gave the isomer ratio: cis, 6.7% and trans, 93.3%.

EXAMPLE 44

To a solution of ethyl chrysanthemate (1.0 g, composition: cis, 88.3% and trans, 11.7%) in 1,2-dichloroethane (9 g) was added thiobenzoic acid (108 mg). Irradiation with a high pressure mercury lamp (100 W) was made for 3 hours. After the reaction was over, similar after-treatment as in Example 19 was applied to obtain ethyl chrysanthemate (960 mg). The isomer ratio of the product was cis, 38.3% and trans, 61.7%.

EXAMPLE 45

To a solution of chrysanthemic acid chloride (1.0 g, composition: cis, 17.3% and trans, 82.7%) in benzene (10 g) was added bromine (90 mg) at room temperature under a nitrogen atmosphere. Irradiation with a xenon lamp (500 W, Pyrex glass filter) was made for 30 minutes. After the irradiation was over, similar after-treatment as in Example 21 was applied to obtain ethyl chrysanthemic acid chloride (0.8 g), which was converted to ester with 2-octanol in a usual manner. Gas chromatography assay gave the isomer ratio: cis, 8.7%; and trans, 91.3%.

EXAMPLE 46

Example 45 was repeated except that phosphorus tribromide (70 mg) was used in place of the bromine to obtain chrysanthemic acid chloride (0.9 g). The isomer ratio of the product was cis, 10.7% and trans, 89.3%.

EXAMPLE 47

To a solution of cis chrysanthemic acid chloride (1.0 g) in chlorobenzene (9 g) was added thiosalicylic acid (125 mg). Irradiation with a xenon lamp (500 W) was made for 3 hours. After the reaction was over, the compound obtained was converted to ethyl chrysanthemate in a usual manner. The isomer ratio of the product was cis, 20.7%; and trans, 79.3%.

EXAMPLE 48

To a solution of chrysanthemic anhydride (1.45 g, composition: cis, 19.4% and trans, 80.6%) in toluene (13 g) was added phosphorus tribromide (0.37 g) under a nitrogen atmosphere. Irradiation with a xenon lamp (500 W) was made for one hour at 70° C. under stirring. After the irradiation was over, the product was hydrolyzed. Gas chromatography assay gave the isomer ratio: cis, 9.5% and trans, 90.5%.

EXAMPLE 49

To a solution of the same chrysanthemic anhydride (2.05 g) as used in Example 48 in toluene (18 g) was added thiocresol (240 mg) under a nitrogen atmosphere. Irradiation with a high pressure mercury lamp (100 W) was made for one hour at 80° C. under stirring. After the irradiation was over, similar after-treatment as in Example 48 was applied. The isomer ratio of the product was cis, 6.0%; and trans, 94.0%.

COMPARATIVE EXAMPLE 1

To a solution of the same levo-rotatory chrysanthemic acid (10 g) as used in Example 1 in toluene (15 g) was added dropwise over 40 minutes a solution (16.8 g) of hydrogen bromide (4.3 wt %)-acetic acid (16%)-toluene (79.7%) at room temperature under a nitrogen atmosphere with stirring. After the addition was over, similar after-treatment as in Example 1 was applied. The optical isomer ratio of the product was (+)-cis, 2.3%; (−)-cis, 5.0%; (+)-trans, 22.3%; and (−)-trans, 70.4%.

COMPARATIVE EXAMPLE 2

(+)-Cis chrysanthemic acid (1.0 g) and toluene (9 g) were charged in a flask (20 ml) under a nitrogen atmosphere and then phosphorus tribromide (0.24 g) was added dropwise under stirring at 20° C. After stirring was effected for one hour keeping the temperature as above, the optical isomer ratio of the product was observed: (+)-cis, 6.9%; (−)-cis, 4.8%; (+)-trans, 44.6%; and (−)-trans, 43.7%.

COMPARATIVE EXAMPLE 3

To a solution of the same levo-rotatory chrysanthemic acid (10 g) as used in Example 1 in toluene (90 g) was added dropwise boron tribromide (1.5 g) under a nitrogen atmosphere, and the solution was stirred at 70° C. for 2 hours. After the reaction was over, similar after-treatment as in Example 1 was applied to obtain chrysanthemic acid (6.1 g). The optical isomer ratio of the product was (+)-cis, 2.5%; (−)-cis, 4.4%; (+)-trans, 41.7%; and (−)-trans, 51.4%.

COMPARATIVE EXAMPLE 4

To a solution of levo-rotatory chrysanthemic acid (5.0 g, composition: (+)-cis, 3.0%; (−)-cis, 22.0%; (+)-trans, 11.8%; and (−)-trans, 63.2%) in toluene (11.7 g) was added aluminum tribromide (0.12 g) at 15°–20° C. and the mixture was stirred for 30 minutes. The optical isomer ratio of the product was (+)-cis, 2.9%; (−)-cis, 4.6%; (+)-trans, 26.5%; and (−)-trans, 65.9%.

COMPARATIVE EXAMPLE 5

To a solution of the same levo-rotatory chrysanthemic acid (1 g) as used in Example 1 in toluene (10 g) was added acetyl bromide (220 mg) at room temperature under a nitrogen atmosphere and the mixture was stirred for 30 minutes. The optical isomer ratio of the product was (+)-cis, 3.0%; (−)-cis, 19.0%; (+)-trans, 10.5%; and (−)-trans, 67.5%.

COMPARATIVE EXAMPLE 6

To a solution of the same levo-rotatory chrysanthemic acid (10 g) as used in Example 12 in toluene (90 g) was added dropwise a solution of boron tribromide (0.25 g) under a nitrogen atmosphere and the mixture was stirred for 30 minutes at 25° C. After the reaction was over, similar after-treatment as in Example 12 was applied. The optical isomer ratio of the product was (+)-cis, 2.5%; (−)-cis, 3.5%; (+)-trans, 38.0%; and (−)-trans, 56.0%.

COMPARATIVE EXAMPLE 7

To a solution of the same levo-rotatory ethyl chrysanthemate (1.0 g) as used in Example 12 in toluene (10 g) was added t-butyl bromide (67 mg) under a nitrogen atmosphere and the mixture was stirred for 30 minutes. After the reaction was over, similar after-treatment as in Example 12 was applied. The optical isomer ratio of the product was (+)-cis, 2.6%; (−)-cis, 14.0%; (+)-trans, 11.2%; and (−)-trans, 72.2%.

COMPARATIVE EXAMPLE 8

Example 1 was repeated except that stirring was made for 30 minutes in the absence of a high pressure mercury lamp. Gas chromatography assay of the product gave isomer ratio: cis, 21.9% and trans, 78.1%.

COMPARATIVE EXAMPLE 9

In a flask (20 ml) was charged cis chrysanthemic acid (1.0 g) and toluene (9 g) under a nitrogen atmosphere and thereto was added phosphorus tribromide (0.24 g) dropwise at 20° C. under stirring. Stirring was continued for one hour keeping the same temperature as above. The isomer ratio of the product was cis, 11.7% and trans, 88.3%.

COMPARATIVE EXAMPLE 10

To a solution of the same chrysanthemic acid (2.0 g) as used in Example 30 in toluene (18 ml) was added a solution of boron tribromide (24 mg) in toluene (2.2 ml) at room temperature under a nitrogen atmosphere. After the addition was over, the mixture was stirred for 10 minutes before a part of the reaction solution was sampled. Stirring was further continued for 2 hours and 20 minutes, before sampling. The samples were converted to ethyl ester in a usual manner. Gas chromatography assay gave the isomer ratios as follows:
cis/trans=20.6/79.4 at 10 minutes after the addition.
cis/trans=10.9/89.1 at 1.5 hours after the addition.

COMPARATIVE EXAMPLE 11

To a solution of the same cis chrysanthemic acid (2.0 g) as used in Example 31 in toluene (20 ml) was added a solution of aluminum tribromide (52 mg) in toluene (2.2 ml) at room temperature under a nitrogen atmosphere. After the addition was over, the mixture was stirred for 10 minutes before a part of the reaction solution was sampled. Stirring was continued for further 50 minutes. Conversion to ethyl ester was made in a usual manner. Gas chromatography assay gave the following cis/trans ratios:
cis/trans=51.7/48.3 at 10 minutes after the addition.
cis/trans=7.0/93.0 at one hour after the addition.

COMPARATIVE EXAMPLE 12

To a solution of the same chrysanthemic acid (1 g) as used in Example 32 in toluene (10 g) was added acetyl bromide (220 mg) at room temperature under a nitrogen atmosphere. After the addition was over, the solution was stirred for 30 minutes.
The isomer ratio of the product was cis, 21.0% and trans, 79.0%.

COMPARATIVE EXAMPLE 13

To a solution of the same ethyl chrysanthemate (2 g) as used in Example 37 in dioxane (20 ml) was added a solution of boron tribromide (41 mg) in dioxane (2.3 ml). After the addition was over, the solution was stirred for one hour before a part thereof was sampled. Stirring was continued for further one hour. Gas chromatography assay gave the following results:
cis/trans=25.0/75.0 at one hour after the addition.
cis/trans=7.0/93.0 at two hours after the addition.

COMPARATIVE EXAMPLE 14

To a solution of the same ethyl chrysanthemate (1.0 g) as used in Example 5 in toluene (10 g) was added t-butyl bromide (67 mg) at room temperature under a nitrogen atmosphere and the mixture was stirred for 30 minutes.

After the reaction was over, similar after-treatment as in Example 5 was applied. The isomer ratio of the product was cis, 16.6% and trans, 83.4%.

We claim:

1. A process for racemization of optically active chrysanthemic acid or its derivatives which comprises allowing optically active chrysanthemic acid or its derivatives of the formula

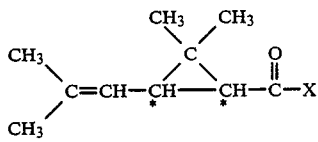

wherein X represents a hydroxyl group, a halogen atom, a $C_{1-20}$ alkoxy group or a 2,2-dimethyl-3-isobutenylcyclopropane carboxyl group and * mark shows asymmetric carbon atoms, to react, in the presence of ultra violet light, with at least one bromine compound selected from the group consisting of hydrogen bromide, phosphorus bromide compounds, boron bromide compounds, aluminum bromide compounds, carboxylic acid bromides, tert.carbon-bromine compounds, N-bromine compounds, Si-bromine compounds, S-bromine compounds, and halo-bromine compounds or SH-compounds.

2. A process according to claim 1 wherein the bromine compound is hydrogen bromide, phosphorus bromide compound, boron bromide compound or aluminum bromide compound.

3. A process according to claim 2 wherein the phosphorus bromide compound is phosphorus tribromide, phosphorus pentabromide or phosphorus oxybromide.

4. A process according to claim 2 wherein the boron bromide is boron tribromide.

5. A process according to claim 2 wherein the aluminum bromide is aluminum tribromide.

6. A process according to claim 1 wherein the carboxylic acid bromide is one having $C_{1-18}$.

7. A process according to claim 1 wherein the tert.-carbon-bromine compound is one having $C_{3-19}$.

8. A process according to claim 1 wherein the N-bromine compound is N-bromoimide or N-bromoamide.

9. A process according to claim 1 wherein the Si-bromine compound is alkylsilyl bromide or silyl tetrabromide.

10. A process according to claim 1 wherein the S-bromine compound is thionyl bromide, sulfuryl bromide, arylsulfonyl bromide, alkylsulfonyl bromide or arylsulfenyl bromide.

11. A process according to claim 1 wherein the halo-bromine compound is bromine, iodine monobromide or iodine tribromide.

12. A process according to claim 1 wherein the SH compound is thiol, carbothioic acid or dithioic acid.

13. A process according to claim 1 wherein the light is ultra violet ray of 200–400 nm.

14. A process according to claim 13 wherein a source of the ray is a high pressure mercury lamp, a xenon lamp or a low pressure mercury lamp.

15. A process for preparing trans-chrysanthemic acid or its derivatives which comprises allowing cis- or cis/-trans mixed-chrysanthemic acid or its derivatives of the formula

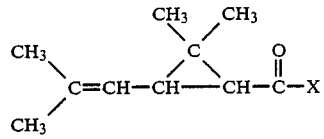

wherein X represents a hydroxyl group, a halogen atom, a $C_{1-20}$ alkoxy group or a 2,2-dimethyl-3-isobutenyl cyclopropane carboxyl group, to react, in the presence of ultra violet light, with at least one bromine compound selected from the group consisting of hydrogen bromide, phosphorus bromide compounds, boron bromide compounds, aluminum bromide compounds, carboxylic acid bromides, tert.carbon-bromine compounds, N-bromine compounds, Si-bromine compounds, S-bromine compounds and halo-bromine compounds or SH-compounds.

16. A process according to claim 15 wherein the bromine compound is hydrogen bromide, phosphorus bromide compound, boron bromide compound or aluminum bromide compound.

17. A process according to claim 16 wherein the phosphorus bromide compound is phosphorus tribromide, phosphorus pentabromide or phosphorus oxybromide.

18. A process according to claim 16 wherein the boron bromide is boron tribromide.

19. A process according to claim 16 wherein the aluminum bromide is aluminum tribromide.

20. A process according to claim 15 wherein the carboxylic acid bromide is one having $C_{1-18}$.

21. A process according to claim 15 wherein the tert.carbon-bromine compound is one having $C_{3-19}$.

22. A process according to claim 15 wherein the N-bromine compound is N-bromoimide or N-bromoamide.

23. A process according to claim 15 wherein the Si-bromine compound is alkylsilyl bromide or silyl tetrabromide.

24. A process according to claim 15 wherein the S-bromine compound is thionyl bromide, sulfuryl bromide, arylsulfonyl bromide, alkylsulfonyl bromide or arylsulfenyl bromide.

25. A process according to claim 15 wherein the halo-bromine compound is bromine, iodine monobromide or iodine tribromide.

26. A process according to claim 15 wherein the SH compound is thiol, carbothioic acid or dithioic acid.

27. A process according to claim 15 wherein the light is ultra violet ray of 200–400 nm.

28. A process according to claim 27 wherein a source of the ray is a high pressure mercury lamp, a xenon lamp or a low pressure mercury lamp.

* * * * *